(12) United States Patent
Kapur et al.

(10) Patent No.: US 9,102,819 B2
(45) Date of Patent: Aug. 11, 2015

(54) POLYOLEFIN COMPOSITION

(71) Applicant: Dow Global Technologies LLC, Midland, MI (US)

(72) Inventors: Mridula Kapur, Lake Jackson, TX (US); Mehmet Demirors, Pearland, TX (US); Philip P. Fontaine, Houston, TX (US); Douglas S. Ginger, Houston, TX (US); David T. Gillespie, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 35 days.

(21) Appl. No.: 14/142,014

(22) Filed: Dec. 27, 2013

(65) Prior Publication Data

US 2015/0148491 A1 May 28, 2015

Related U.S. Application Data

(60) Provisional application No. 61/746,151, filed on Dec. 27, 2012.

(51) Int. Cl.
*C08L 23/04* (2006.01)
*C08L 23/00* (2006.01)
*C08L 23/08* (2006.01)
*C08L 23/06* (2006.01)

(52) U.S. Cl.
CPC ............... *C08L 23/08* (2013.01); *C08L 23/06* (2013.01); *C08L 2205/025* (2013.01); *C08L 2205/03* (2013.01)

(58) Field of Classification Search
CPC ... C08L 23/08; C08L 23/04; C08L 2205/025; C08L 2205/03
USPC ................................................ 525/191, 240
See application file for complete search history.

(56) References Cited

U.S. PATENT DOCUMENTS

| 5,631,069 A | * | 5/1997 | Wooster et al. ............... 428/220 |
| 6,323,285 B1 | * | 11/2001 | Johnston et al. .............. 525/242 |
| 2011/0282018 A1 | | 11/2011 | Klosin et al. | |

FOREIGN PATENT DOCUMENTS

WO    2007136496 A2    11/2007

OTHER PUBLICATIONS

Balke, Chromatography of Polymers, 1992, Chapter 12, p. 180-198.
Balke, Chromatography Polym., 1992, Chapter 13, p. 199-219.
Karjala, Annual Technical Conference—Society of Plastics Engineers, 2008, 66th, 887-891.
Monrabal, Macromol. Symp., 2007, vol. 257, p. 71-79.
Yau, Macromol. Symp., 2007, vol. 257, p. 29-45.
Zimm, J. Chem. Phys., 1948, vol. 16, p. 1099-1116.

* cited by examiner

*Primary Examiner* — Nathan M Nutter

(57) ABSTRACT

The instant invention provides a polyolefin composition suitable for injection molding applications, and method of making such injection molded articles. The polyolefin composition suitable for injection molding applications comprises: an ethylene/α-olefin interpolymer composition comprising: (a) from 25 to 50 percent by weight of a first ethylene/α-olefin copolymer fraction having a density in the range of from 0.924 to 0.937 g/cm$^3$, a melt index ($I_2$) in the range of from 0.03 to 0.3 g/10 min, (b) from 50 to 75 percent by weight of a second ethylene homopolymer fraction having a density in the range of from greater than 0.960 g/cm$^3$, a melt index ($I_2$) in the range of from 100 to 180 g/10 minutes, wherein said ethylene/α-olefin interpolymer composition has a density in the range of from 0.950 to 0.958 g/cm$^3$, a melt index ($I_2$) in the range of from 1.0 g/10 min to 3.5 g/10 min, a zero shear viscosity ratio (ZSVR) in the range of from 1.01 to 2.5, a molecular weight distribution ($M_w/M_n$) in the range of from 2.0 to 4.0, and tan delta at 0.1 radian/second and 190° C. in the range of from 9 to 50.

4 Claims, 1 Drawing Sheet

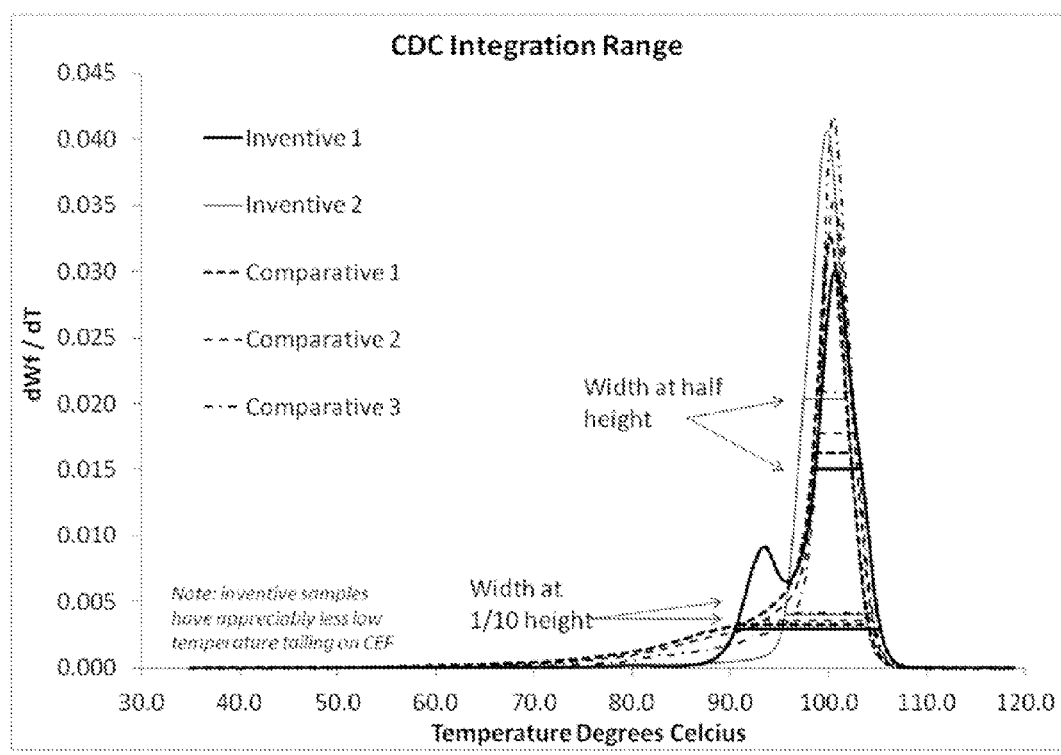

POLYOLEFIN COMPOSITION

REFERENCE TO RELATED APPLICATIONS

The present application claims the benefit of U.S. Provisional Application No. 61/746,151, filed on Dec. 27, 2012.

FIELD OF INVENTION

The instant invention relates to a polyolefin composition suitable for injection molding or compression molding applications, and method of producing the same.

BACKGROUND OF THE INVENTION

The use of polymeric materials to manufacture molded articles, such as closure devices and containers, is generally known. Different methods may be employed to manufacture closure devices, such as bottle caps, or containers, such as bottles. For example, such closure devices may be manufactured via compression molding or injection molding processes; or in the alternative, containers may be manufactured via blow molding, injection blow molding, or injection stretch blow molding.

In compression molding process, a two-piece mold provides a cavity having the shape of a desired molded article. The mold is heated. An appropriate amount of molten molding compound from an extruder is loaded into the lower half of the mold. The two parts of the mold are brought together under pressure. The molding compound, softened by heat, is thereby welded into a continuous mass having the shape of the cavity. If the molding compound is a thermosetting material, the continuous mass may be hardened via further heating, under pressure, in the mold. If the molding compound is a thermoplastic material, the continuous mass may be hardened via chilling, under pressure, in the mold.

In injection molding process, molding compound is fed into an extruder via a hopper. The extruder conveys, heats, melts, and pressurizes the molding compound to a form a molten stream. The molten stream is forced out of the extruder through a nozzle into a relatively cool mold held closed under pressure thereby filing the mold. The melt cools and hardens until fully set-up. The mold then opens and the molded part is removed.

In blow molding process, for example injection blow molding, the molding compound is melted, and then, it is formed into a tube or parison. The ends of the tube or parison is sealed, except for an area in which the blowing air can enter. The sealed tube or parison is inflated inside of a mold thereby taking the shape of the mold. The molded article is cooled, and then ejected from the mold. If necessary, the molded article is then trimmed.

In general, a closure device, such as a soda bottle cap, should be strong enough to withstand the pressure, e.g. of a carbonated drink, and yet soft enough to provide an excellent seal on the bottle without the need for an inner liner. Additionally, a closure device, such as a soda bottle cap, should generally possess good environmental stress crack resistance, good impact strength, good removal torque, and good strip torque. Different techniques have been employed to provide for such closure devices having acceptable properties.

For example, the use of a polypropylene polymer as a bottle cap closure for the needed strength with an inner liner, which may be comprised of soft ethylene/vinyl acetate (EVA), polyvinyl chloride (PVC), butyl rubber, etc., is also generally well known. However, this two-part construction is costly because of the need for an inner liner. Furthermore, it would be easier and more convenient to use a one-piece closure, without a liner.

In attempts to eliminate the need for a two-part cap construction, the use of different blends of polymers has been suggested. However, there is still a need for polymer composition that can be molded into closure devices having acceptable properties, such as no need for liners to facilitate a seal, acceptable taste and odor, satisfactory stress crack resistance, and impact strength to prevent cap failure.

SUMMARY OF THE INVENTION

The instant invention provides a polyolefin composition suitable for injection molding applications, and method of making such injection molded articles.

In one embodiment, the instant invention provides a polyolefin composition suitable for injection molding applications comprising: an ethylene/α-olefin interpolymer composition comprising: (a) from 25 to 50 percent by weight of a first ethylene/α-olefin copolymer fraction having a density in the range of from 0.924 to 0.937 g/cm$^3$, a melt index (I$_2$) in the range of from 0.03 to 0.3 g/10 min, (b) from 50 to 75 percent by weight of a second ethylene homopolymer fraction having a density in the range of from greater than 0.960 g/cm$^3$, a melt index (I$_2$) in the range of from 100 to 180 g/10 minutes, wherein said ethylene/α-olefin interpolymer composition has a density in the range of from 0.950 to 0.958 g/cm$^3$, a melt index (I$_2$) in the range of from 1.0 g/10 min to 3.5 g/10 min, a zero shear viscosity ratio (ZSVR) in the range of from 1.01 to 2.5, a molecular weight distribution (M$_w$/M$_n$) in the range of from 2.0 to 4.0, and tan delta at 0.1 radian/second and 190° C. in the range of from 9 to 50, wherein said ethylene/α-olefin interpolymer composition has at least 1 peak on elution profile via crystallization elution fractionation (CEF) procedure, wherein said peak comprises at least 95 weight percent of the total area of the elution profile, wherein said elution temperature peak is at an elution temperature greater than 95° C., and wherein the width of the elution temperature peak at 50 percent peak height is greater than 4° C. and less than 6° C., and wherein the standard deviation of the temperature is less than 6° C.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 1 illustrates the elution profile via crystallization elution fractionation (CEF) procedure for Inventive Examples and Comparative Examples.

DETAILED DESCRIPTION OF THE INVENTION

The instant invention provides a polyolefin composition suitable for injection molding applications, and method of making such injection molded articles.

In one embodiment, the instant invention provides a polyolefin composition suitable for injection molding applications comprising: an ethylene/α-olefin interpolymer composition comprising: (a) from 25 to 50 percent by weight of a first ethylene/α-olefin copolymer fraction having a density in the range of from 0.924 to 0.937 g/cm$^3$, a melt index (I$_2$) in the range of from 0.03 to 0.3 g/10 min, (b) from 50 to 75 percent by weight of a second ethylene homopolymer fraction having a density in the range of from greater than 0.960 g/cm$^3$, a melt index ($I_2$) in the range of from 100 to 180 g/10 minutes, wherein said ethylene/α-olefin interpolymer composition has a density in the range of from 0.950 to 0.958 g/cm$^3$, a melt index ($I_2$) in the range of from 1.0 g/10 min to 3.5 g/10 min, a zero shear viscosity ratio (ZSVR) in the range of from 1.01 to 2.5, a molecular weight distribution ($M_w/M_n$) in the range of from 2.0 to 4.0, and tan delta at 0.1 radian/second and 190° C. in the range of from 9 to 50, wherein said ethylene/α-olefin interpolymer composition has at least 1 peak on elution profile via crystallization elution fractionation (CEF) procedure, wherein said peak comprises at least 95 weight percent of the total area of the elution profile, wherein said elution temperature peak is at an elution temperature greater than 95° C., and wherein the width of the elution temperature peak at 50 percent peak height is greater than 4° C. and less than 6° C., and wherein the standard deviation of the temperature is less than 6° C.

The polyolefin composition may further comprise additional components such as one or more other polymers. For example the polyolefin composition may further comprise one or more ethylene polymers, or one or more propylene based polymers, or combinations thereof.

In one embodiment, one or more ethylene/α-olefin interpolymer compositions and one or more propylene/α-olefin interpolymer compositions, as described herein, may be blended via any method known to a person of ordinary skill in the art including, but not limited to, dry blending, and melt blending via any suitable equipment, for example, an extruder, to produce the inventive injection molding composition.

The polyolefin composition may further comprise additional components such as one or more additives. Such additives include, but are not limited to, antistatic agents, color enhancers, dyes, lubricants, fillers such as $TiO_2$ or $CaCO_3$, opacifiers, nucleators, pigments, primary anti-oxidants, secondary anti-oxidants, processing aids, UV stabilizers, antiblocks, slip agents, tackifiers, fire retardants, anti-microbial agents, odor reducer agents, anti-fungal agents, and combinations thereof. The polyolefin composition may contain from about 0.01 to about 10 percent by the combined weight of such additives, based on the weight of the ethylene-based polymer composition including such additives.

Ethylene/α-Olefin Interpolymer Composition

The ethylene/α-olefin interpolymer composition comprising: (a) from 25 to 50 percent by weight of a first ethylene/α-olefin copolymer fraction having a density in the range of from 0.924 to 0.937 g/cm$^3$, a melt index ($I_2$) in the range of from 0.03 to 0.3 g/10 min, (b) from 50 to 75 percent by weight of a second ethylene homopolymer fraction having a density in the range of from greater than 0.960 g/cm$^3$, a melt index ($I_2$) in the range of from 100 to 180 g/10 minutes, wherein said ethylene/α-olefin interpolymer composition has a density in the range of from 0.950 to 0.958 g/cm$^3$, a melt index ($I_2$) in the range of from 1.0 g/10 min to 3.5 g/10 min, a zero shear viscosity ratio (ZSVR) in the range of from 1.01 to 2.5, a molecular weight distribution ($M_w/M_n$) in the range of from 2.0 to 4.0, and tan delta at 0.1 radian/second and 190° C. in the range of from 9 to 50, wherein said ethylene/α-olefin interpolymer composition has at least 1 peak on elution profile via crystallization elution fractionation (CEF) procedure, wherein said peak comprises at least 95 weight percent of the total area of the elution profile, wherein said elution temperature peak is at an elution temperature greater than 95° C., and wherein the width of the elution temperature peak at 50 percent peak height is greater than 4° C. and less than 6° C., and wherein the standard deviation of the temperature is less than 6° C.

The ethylene/α-olefin interpolymer composition is further characterized by one or more of the followings:
a. has a vinyl unsaturation of less than 0.15 vinyls per one thousand carbon atoms present in the backbone of the ethylene/α-olefin interpolymer composition; and/or
b. has a tan delta at 0.1 radian/second, determined at 190° C., in the range of from 9 to 50;
c. has Comonomer Distribution Constant (CDC) in the range of from 150 or less;
d. has a environmental stress crack resistance (ESCR) failure time F50 of at least 150 hours, determined by ASTM 1693 Method B in aqueous 10% Igepal; and/or
e. has a oligomers content, i.e. $C_{10}$-$C_{44}$, of less than 100 ppm.

The ethylene/α-olefin interpolymer composition comprises (a) less than or equal to 100 percent, for example, at least 70 percent, or at least 80 percent, or at least 90 percent, of the units derived from ethylene; and (b) less than 30 percent, for example, less than 25 percent, or less than 20 percent, or less than 10 percent, by weight of units derived from one or more α-olefin comonomers. The term "ethylene/α-olefin interpolymer composition" refers to a polymer that contains more than 50 mole percent polymerized ethylene monomer (based on the total amount of polymerizable monomers) and, optionally, may contain at least one comonomer.

The α-olefin comonomers typically have no more than 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-hexene and 1-octene.

The ethylene/α-olefin interpolymer composition is characterized by having a Comonomer Distribution Constant (CDC) in the range of from 150 or less, for example from 75 to 150, or in the alternative, from 90 to 135.

The ethylene-based polymer composition is characterized by having a zero shear viscosity ratio (ZSVR) in the range of from 1.01 to 2.5, for example from 1.15 to 2.5, or in the alternative from 1.15 to 2.0, or in the alternative from 1.2 to 1.8.

The ethylene/α-olefin interpolymer composition is characterized by having a tan delta at 0.1 radian/second, determined at 190° C., in the range of from 9 to 50, for example from 9 to 40, or from 9 to 30, or from 9 to 25, or from 10 to 25, or from 10 to 30, or from 10 to 40.

The ethylene/α-olefin interpolymer composition has a density in the range of 0.950 to 0.958 g/cm$^3$, for example from 0.950 to 0.956 g/cm$^3$. For example, the density can be from a lower limit of 0.950, 0.951, or 0.952 g/cm$^3$ to an upper limit of 0.955, 0.956, 0.957, or 0.958 g/cm$^3$.

The ethylene/α-olefin interpolymer composition comprising from 25% to 50% percent by weight, preferably from 30% to 45%, more preferably from 33% to 43%, most preferably from 35% to 42% of the first ethylene/α-olefin copolymer fraction.

The first ethylene/α-olefin copolymer fraction has a density in the range of 0.924 to 0.937 g/cm$^3$, for example from 0.925 to 0.936 g/cm$^3$. For example, the density can be from a lower limit of 0.924, 0.925, 0.926, or 0.927 g/cm$^3$ to an upper limit of 0.934, 0.935, 0.936, or 0.937 g/cm$^3$.

The second ethylene/α-olefin homopolymer fraction has a density in the range of greater than 0.960 g/cm$^3$. For example, the density can be from greater than 0.960, 0.963, 0.965, 0.967, 0.970 g/cm$^3$. The density of the second ethylene/α-olefin homopolymer fraction can be approximated based on the density of a polymer prepared in a single reactor under the same polymerisation conditions of the second ethylene/α-olefin homopolymer fraction in the absence of the first ethylene/α-olefin copolymer fraction.

The ethylene/α-olefin interpolymer composition has a molecular weight distribution ($M_w/M_n$) in the range of from 2.0 to 4.0. For example, the molecular weight distribution ($M_w/M_n$) can be from a lower limit of 2.0, 2.1, or 2.2 to an upper limit of 2.6, 2.8, 3.0, 3.5, or 4.0.

The first ethylene/α-olefin copolymer fraction has a molecular weight distribution ($M_w/M_n$) in the range of from 1.5 to 3.5, for example from 2 to 3. For example, the molecular weight distribution ($M_w/M_n$) can be from a lower limit of 1.5, 1.7, 2.0, 2.1, or 2.2 to an upper limit of 2.5, 2.6, 2.8, 3.0, or 3.5.

The second ethylene/α-olefin homopolymer fraction has a molecular weight distribution ($M_w/M_n$) in the range of from 1.5 to 3.0, for example from 2 to 3. For example, the molecular weight distribution ($M_w/M_n$) can be from a lower limit of 1.5, 1.7, 2.0, 2.1, or 2.2 to an upper limit of 2.5, 2.6, 2.8, or 3.0.

The ethylene/α-olefin interpolymer composition has a melt index ($I_2$) (at 190° C./2.16 kg) in the range of from 1.0 to 3.5 g/10 minutes, for example from 1.5 to 3.0 g/10 minutes, or from 1.5 to 2.5 g/10 minutes. For example, the melt index ($I_2$ at 190° C./2.16 kg) can be from a lower limit of 1.0, 1.3, 1.5, or 1.7 g/10 minutes to an upper limit of 2.5, 2.7, 3.0, 3.3, or 3.5 g/10 minutes.

The first ethylene/α-olefin copolymer fraction has a melt index ($I_2$) (at 190° C./2.16 kg) in the range of from 0.03 to 0.3 g/10 minutes, for example from 0.05 to 0.25 g/10 minutes, or from 0.05 to 0.2 g/10 minutes, or from 0.05 to 0.15 g/10 minutes.

The ethylene/α-olefin interpolymer composition has vinyl unsaturation of less than 0.15, for example equal or less than 0.12, or less than 0.1 vinyls per one thousand carbon atoms present in the backbone of the ethylene-based polymer composition.

The ethylene/α-olefin interpolymer composition may further comprise additional components such as one or more additives. Such additives include, but are not limited to, antistatic agents, color enhancers, dyes, lubricants, fillers such as $TiO_2$ or $CaCO_3$, opacifiers, nucleators, processing aids, pigments, primary anti-oxidants, secondary anti-oxidants, processing aids, UV stabilizers, anti-blocks, slip agents, tackifiers, fire retardants, anti-microbial agents, odor reducer agents, anti-fungal agents, and combinations thereof. The ethylene/α-olefin interpolymer composition may contain from about 0.1 to about 10 percent by the combined weight of such additives, based on the weight of the ethylene-based polymer composition including such additives.

In one embodiment, ethylene/α-olefin interpolymer composition has at least 1 peak on elution profile via crystallization elution fractionation (CEF) procedure, wherein said peak comprises at least 95 weight percent of the total area of the elution profile, wherein said elution temperature peak is at an elution temperature greater than 95° C., and wherein the width of the elution temperature peak at 50 percent peak height is greater than 4° C. and less than 6° C., and wherein the standard deviation of the temperature is less than 6° C.

Any conventional polymerization processes may be employed to produce the ethylene/α-olefin interpolymer composition. Such conventional polymerization processes include, but are not limited to, solution polymerization process, using one or more conventional reactors e.g. loop reactors, isothermal reactors, stirred tank reactors, batch reactors in parallel, series, and/or any combinations thereof.

The ethylene/α-olefin interpolymer composition may, for example, be produced via solution phase polymerization process using one or more loop reactors, isothermal reactors, and combinations thereof.

In general, the solution phase polymerization process occurs in one or more well-mixed reactors such as one or more isothermal loop reactors or one or more adiabatic reactors at a temperature in the range of from 115 to 250° C.; for example, from 115 to 200° C., and at pressures in the range of from 300 to 1000 psi; for example, from 400 to 750 psi. In one embodiment in a dual reactor, the temperature in the first reactor is in the range of from 115 to 190° C., for example, from 115 to 150° C., and the second reactor temperature is in the range of 150 to 250° C., for example, from 170 to 225° C. In another embodiment in a single reactor, the temperature in the reactor is in the range of from 115 to 250° C., for example, from 115 to 225° C. The residence time in solution phase polymerization process is typically in the range of from 2 to 30 minutes; for example, from 10 to 20 minutes. Ethylene, solvent, hydrogen, one or more catalyst systems, optionally one or more cocatalysts, and optionally one or more comonomers are fed continuously to one or more reactors. Exemplary solvents include, but are not limited to, isoparaffins. For example, such solvents are commercially available under the name ISOPAR E from ExxonMobil Chemical Co., Houston, Tex. The resultant mixture of the ethylene/alpha-olefin interpolymer and solvent is then removed from the reactor and the ethylene/alpha-olefin interpolymer is isolated. Solvent is typically recovered via a solvent recovery unit, i.e. heat exchangers and vapor liquid separator drum, and is then recycled back into the polymerization system.

In one embodiment, the ethylene/α-olefin interpolymer composition may be produced via solution polymerization in a dual reactor system, for example a dual loop reactor system, wherein ethylene and optionally one or more α-olefins are polymerized in the presence of one or more catalyst systems. Additionally, one or more cocatalysts may be present.

In another embodiment, the ethylene/alpha-olefin interpolymers may be produced via solution polymerization in a single reactor system, for example a single loop reactor system, wherein ethylene and optionally one or more α-olefins are polymerized in the presence of one or more catalyst systems.

An exemplary catalyst system suitable for producing the first ethylene/a olefin interpolymer can be a catalyst system comprising a procatalyst component comprising a metal-ligand complex of formula (IA):

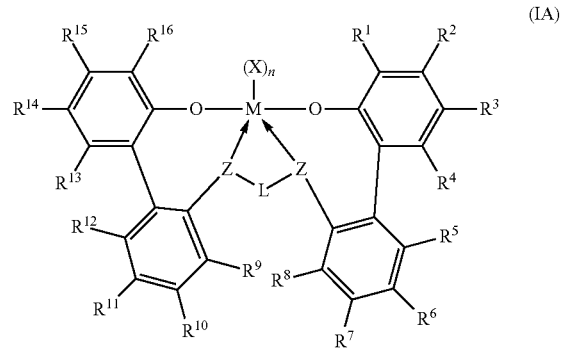

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (IA) is, overall, neutral; and Each Z independently is O, S, N($C_1$-$C_{40}$)hydrocarbyl, or P($C_1$-$C_{40}$)hydrocarbyl; and The Z-L-Z fragment is comprised of formula (II):

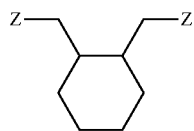

(II)

$R^{1-16}$ are selected from the group consisting of a ($C_1$-$C_{40}$) hydrocarbyl, ($C_1$-$C_{40}$)heterohydrocarbyl, Si($R^C$)$_3$, Ge($R^C$)$_3$, P($R^P$)$_2$, N($R^N$)$_2$, OR$^C$, SR$^C$, NO$_2$, CN, CF$_3$, R$^C$S(O)—, R$^C$S(O)$_2$—, (R$^C$)$_2$C=N—, R$^C$C(O)O—, R$^C$OC(O)—, R$^C$C(O)N(R)—, (R$^C$)$_2$NC(O)—, halogen atom, hydrogen atom, and combination thereof.

Optionally two or more R groups (from $R^{9-13}$ or $R^{4-8}$) can combine together into ring structures, with such ring structures having from 3 to 50 atoms in the ring excluding any hydrogen atoms.

Each of the aryl, heteroaryl, hydrocarbyl, heterohydrocarbyl, Si($R^C$)$_3$, Ge($R^C$)$_3$, P($R^P$)$_2$, N($R^N$)$_2$, OR$^C$, SR$^C$, R$^C$S(O)—, R$^C$S(O)$_2$—, (R$^C$)$_2$C=N—, R$^C$C(O)O—, R$^C$OC(O)—, R$^C$C(O)N(R)—, (R$^C$)$_2$NC(O)—, hydrocarbylene, and heterohydrocarbylene groups independently is unsubstituted or substituted with one or more $R^S$ substituents; and Each $R^S$ independently is a halogen atom, polyfluoro substitution, perfluoro substitution, unsubstituted ($C_1$-$C_{18}$)alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the $R^S$ are taken together to form an unsubstituted ($C_1$-$C_{18}$)alkylene, wherein each R independently is an unsubstituted ($C_1$-$C_{18}$)alkyl.

In one embodiment the catalyst system suitable for producing the first ethylene/α olefin interpolymer can be a catalyst system comprising bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

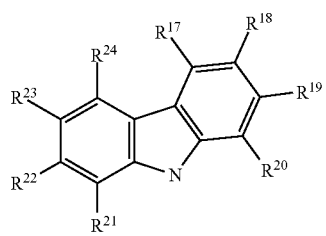

An exemplary catalyst system suitable for producing the second ethylene/α olefin homopolymer can be a catalyst system comprising a procatalyst component comprising a metal-ligand complex of formula (IB):

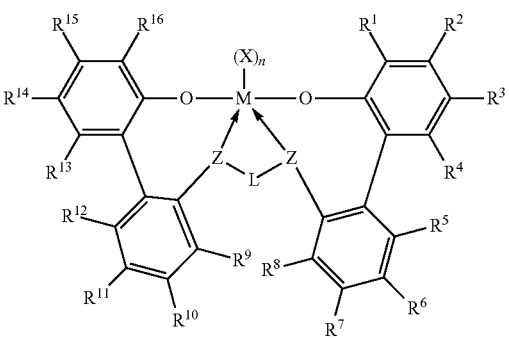

(IB)

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (IB) is, overall, neutral; and Each Z independently is O, S, N($C_1$-$C_{40}$)hydrocarbyl, or P($C_1$-$C_{40}$)hydrocarbyl; and L is ($C_3$-$C_{40}$)hydrocarbylene or ($C_3$-$C_{40}$)heterohydrocarbylene, wherein the ($C_3$-$C_{40}$)hydrocarbylene has a portion that comprises a 3-carbon atom to 10-carbon atom linker backbone linking the Z atoms in formula (IB) (to which L is bonded) and the ($C_3$-$C_{40}$)heterohydrocarbylene has a portion that comprises a 3-atom to 10-atom linker backbone linking the Z atoms in formula (IB), wherein each of the from 3 to 10 atoms of the 3-atom to 10-atom linker backbone of the ($C_3$-$C_{40}$)heterohydrocarbylene independently is a carbon atom or heteroatom, wherein each heteroatom independently is O, S, S(O), S(O)$_2$, Si($R^C$)$_2$, Ge($R^C$)$_2$, P($R^P$), or N($R^N$), wherein independently each $R^C$ is ($C_1$-$C_{30}$)hydrocarbyl, each $R^P$ is ($C_1$-$C_{30}$)hydrocarbyl; and each $R^N$ is ($C_1$-$C_{30}$)hydrocarbyl or absent; and $R^1$, $R^{16}$, or both comprise of formula (III), and preferably $R^1$ and $R^{16}$ are the same; and (III)

$R^{1-24}$ are selected from the group consisting of a ($C_1$-$C_{40}$) hydrocarbyl, ($C_1$-$C_{40}$)heterohydrocarbyl, Si($R^C$)$_3$, Ge($R^C$)$_3$, P($R^P$)$_2$, N($R^N$)$_2$, OR$^C$, SR$^C$, NO$_2$, CN, CF$_3$, R$^C$S(O)—, R$^C$S(O)$_2$—, (R$^C$)$_2$C=N—, R$^C$C(O)O—, R$^C$OC(O)—, R$^C$C(O)N(R)—, (R$^C$)$_2$NC(O)—, halogen atom, hydrogen atom, and combination thereof.

When $R^{22}$ is H, then $R^{19}$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and When $R^{19}$ is H, then $R^{22}$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and Preferably, $R^{22}$ and $R^{19}$ are both a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and When $R^8$ is H, then $R^9$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and When $R^9$ is H, then $R^8$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and Preferably, $R_8$ and $R_9$ are both a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, OR$^C$, SR$^C$, NO$_2$, CN, CF$_3$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)— or halogen atom; and Optionally two or more R groups (from $R^{9-13}$ or $R^{4-8}$) can combine together into ring structures, with such ring structures having from 3 to 50 atoms in the ring excluding any hydrogen atoms.

Each of the aryl, heteroaryl, hydrocarbyl, heterohydrocarbyl, Si$(R^C)_3$, Ge$(R^C)_3$, P$(R^P)_2$, N$(R^N)_2$, OR$^C$, SR$^C$, R$^C$S(O)—, R$^C$S(O)$_2$—, $(R^C)_2$C=N—, R$^C$C(O)O—, R$^C$OC(O)—, R$^C$C(O)N(R)—, $(R^C)_2$NC(O)—, hydrocarbylene, and heterohydrocarbylene groups independently is unsubstituted or substituted with one or more R$^S$ substituents; and Each R$^S$ independently is a halogen atom, polyfluoro substitution, perfluoro substitution, unsubstituted $(C_1$-$C_{18})$alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the R$^S$ are taken together to form an unsubstituted $(C_1$-$C_{18})$alkylene, wherein each R independently is an unsubstituted $(C_1$-$C_{18})$alkyl.

Optionally two or more R groups (from $R^{20-24}$) can combine together into ring structures, with such ring structures having from 3 to 50 atoms in the ring excluding any hydrogen atoms.

In one embodiment the catalyst system suitable for producing the second ethylene/α olefin homopolymer can be a catalyst system comprising ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5-fluoro-3'-methyl-5-(2,4,4-trimethylpentan-2-yl)[1,1'-biphenyl]-2-yl)oxy)hafnium (IV) dimethyl, represented by the following formula:

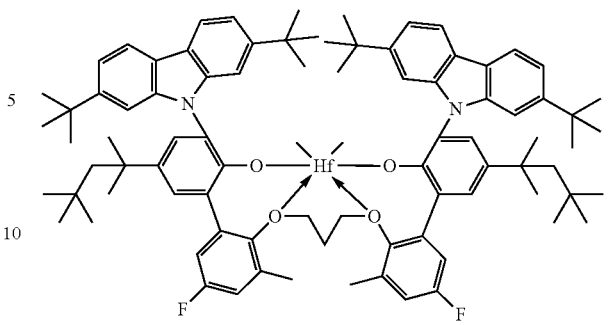

Co-Catalyst Component

The above described catalyst systems can be rendered catalytically active by contacting it to, or combining it with, the activating co-catalyst or by using an activating technique such as those that are known in the art for use with metal-based olefin polymerization reactions. Suitable activating co-catalysts for use herein include alkyl aluminums; polymeric or oligomeric alumoxanes (also known as aluminoxanes); neutral Lewis acids; and non-polymeric, noncoordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 metal compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri($(C_1$-$C_{10})$alkyl)aluminum or tri($(C_6$-$C_{18})$aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris($(C_1$-$C_{20})$hydrocarbyl) borate (e.g., trityl tetrafluoroborate) or a tri($(C_1$-$C_{20})$hydrocarbyl)ammonium tetra($(C_1$-$C_{20})$hydrocarbyl)borane (e.g., bis(octadecyl)methylammonium tetrakis(pentafluorophenyl)borane). As used herein, the term "ammonium" means a nitrogen cation that is a (($(C_1$-$C_{20})$hydrocarbyl)$_4$N$^+$, a (($(C_1$-$C_{20})$hydrocarbyl)$_3$N(H)$^+$, a (($(C_1$-$C_{20})$hydrocarbyl)$_2$N(H)$_2$$^+$, $(C_1$-$C_{20})$hydrocarbylN(H)$_3$$^+$, or N(H)$_4$$^+$, wherein each $(C_1$-$C_{20})$hydrocarbyl may be the same or different.

Exemplary combinations of neutral Lewis acid activating co-catalysts include mixtures comprising a combination of a tri($(C_1$-$C_4)$alkyl)aluminum and a halogenated tri($(C_6$-$C_{18})$aryl)boron compound, especially a tris(pentafluorophenyl) borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex):(tris (pentafluoro-phenylborane): (alumoxane) [e.g., (Group 4 metal-ligand complex):(tris(pentafluoro-phenylborane): (alumoxane)] are from 1:1:1 to 1:10:30, other exemplary embodiments are from 1:1:1.5 to 1:5:10.

Many activating co-catalysts and activating techniques have been previously taught with respect to different metal-ligand complexes in the following: U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425, 872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163, 907. Examples of suitable hydrocarbyloxides are disclosed in U.S. Pat. No. 5,296,433. Examples of suitable Bronsted acid salts for addition polymerization catalysts are disclosed in U.S. Pat. No. 5,064,802; U.S. Pat. No. 5,919,983; U.S. Pat. No. 5,783,512. Examples of suitable salts of a cationic oxidizing agent and a noncoordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, the above described catalyst systems can be activated to form an active catalyst composition by combination with one or more cocatalyst such as a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to modified methyl aluminoxane (MMAO), bis(hydrogenated tallow alkyl)methyl, tetrakis(pentafluorophenyl) borate(1-) amine (RIBS-2), triethyl aluminum (TEA), and any combinations thereof.

In some embodiments, one or more of the foregoing activating co-catalysts are used in combination with each other. An especially preferred combination is a mixture of a tri((C$_1$-C$_4$)hydrocarbyl)aluminum, tri((C$_1$-C$_4$)hydrocarbyl)borane, or an ammonium borate with an oligomeric or polymeric alumoxane compound.

End-Use Applications of the Polyolefin Composition

The polyolefin compositions according to the present invention may be used in injection molding applications.

In application, the inventive polyolefin composition may be used to manufacture shaped articles. Such articles may include, but are not limited to, closure devices such as bottle caps, or container devices such as bottles. Different methods may be employed to manufacture articles such as bottle caps and bottles. Suitable conversion techniques include, but are not limited to, injection molding, injection blow molding, and/or injection stretch blow molding. Such techniques are generally well known.

In injection molding process, the inventive polyolefin composition is fed into an extruder via a hopper. The extruder conveys, heats, melts, and pressurizes the polyolefin composition to a form a molten stream. The molten stream is forced out of the extruder through a nozzle into a relatively cool mold held closed under pressure thereby filling the mold. The melt cools and hardens until fully set-up. The mold then opens and the molded article, for example bottle cap, is removed. The injection molded cap may include a skirt that axially extends from the periphery of a base, and may further include internal threads for securing the cap to a container.

Closure devices such as bottle caps including the inventive polyolefin composition exhibit improved environmental crack resistance. Such bottle caps are adapted to withstand the pressure of carbonated drinks. Such bottle caps further facilitate closure, and sealing of a bottle, that is optimum torque provided by a machine to screw the cap on the bottle, or unsealing a bottle, that is optimum torque provide by a person to unscrew the cap.

The polyolefin composition of the present invention provide improved organoleptic properties due to low levels of unsaturation, i.e. vinyl groups and/or oligomer content.

EXAMPLES

The following examples illustrate the present invention but are not intended to limit the scope of the invention.
Inventive Polyolefin Composition 1

Inventive polyolefin composition 1 (IPC-1) comprises an ethylene-octene interpolymer, having a density of approximately 0.954 g/cm$^3$, a melt index (I$_2$), measured at 190° C. and 2.16 kg, of approximately 2.6 g/10 minutes, an melt flow ratio (I$_{10}$/I$_2$) of approximately 10. Additional properties of IPC-1 were measured, and are reported in Table 2.

IPC-1 was prepared via solution polymerization in adiabatic stirred tank reactors connected in parallel in the presence of a first catalyst system, as described below, in the first reactor and a second catalyst system, as described below, in the second reactor. First ethylene fraction and second ethylene fraction were contacted with each other and blended via solution blended process, and then followed with devolatization and pelletization form IPC-1.

The first catalyst system comprises bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

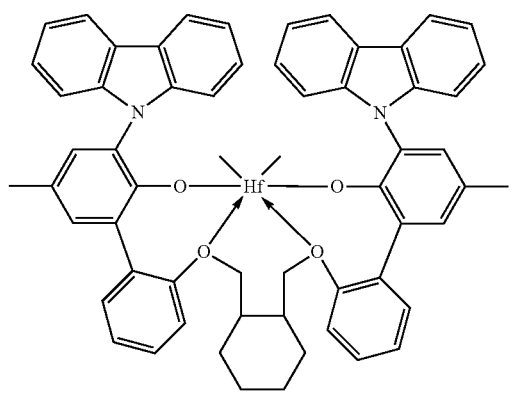

The second catalyst system comprises ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

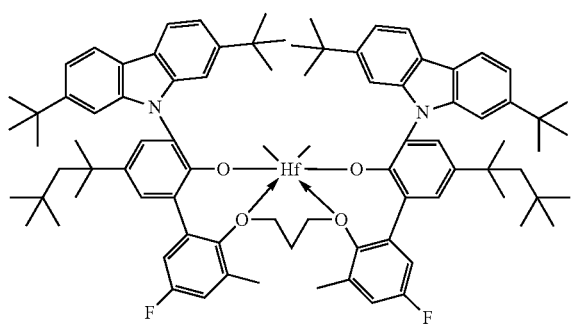

The polymerization conditions for IPC-1 are reported in Table 1. Referring to Table 1, MMAO is modified methyl aluminoxane; and RIBS-2 is bis(hydrogenated tallow alkyl) methyl, tetrakis(pentafluorophenyl)borate(1-) amine, used as cocatalysts.

Inventive Polyolefin Composition 2

Inventive polyolefin composition 2 (IPC-2) comprises an ethylene-octene interpolymer, having a density of approximately 0.953 g/cm³, a melt index ($I_2$), measured at 190° C. and 2.16 kg, of approximately 1.5 g/10 minutes, an melt flow ratio ($I_{10}/I_2$) of approximately 9. Additional properties of IPC-2 were measured, and are reported in Table 2.

IPC-2 was prepared via solution polymerization in adiabatic stirred tank reactors connected in parallel in the presence of a first catalyst system, as described below, in the first reactor and a second catalyst system, as described below, in the second reactor. First ethylene fraction and second ethylene fraction were contacted with each other and blended via solution blended process, and then followed with devolatization and pelletization form IPC-2.

The first catalyst system comprises bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

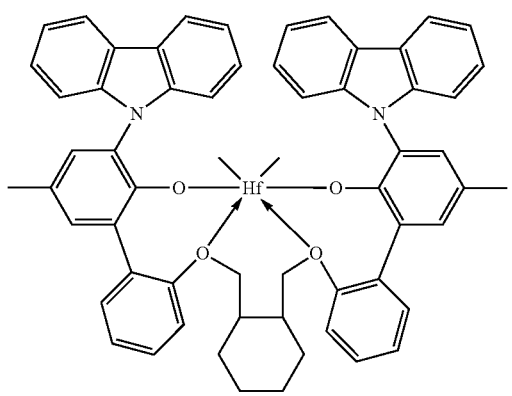

The second catalyst system comprises ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

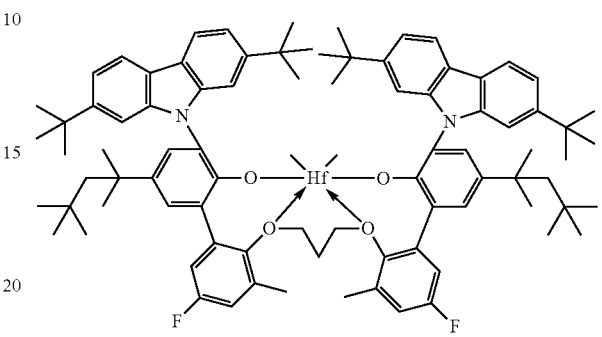

The polymerization conditions for IPC-2 are reported in Table 1. Referring to Table 1, MMAO is modified methyl aluminoxane; and RIBS-2 is bis(hydrogenated tallow alkyl) methyl, tetrakis(pentafluorophenyl)borate(1-) amine, used as cocatalysts.

Comparative Polyolefin Composition 1

Comparative polyolefin composition 1 (CPC-1) comprises an ethylene-hexene interpolymer, having a density of approximately 0.956 g/cm³, a melt index ($I_2$), measured at 190° C. and 2.16 kg, of approximately 1.4 g/10 minutes, an melt flow ratio ($I_{10}/I_2$) of approximately 13. Additional properties of CPC-1 are reported in Table 2. CPC-1 was prepared via gas phase polymerization in a fluidized bed dual reactor system.

Comparative Polyolefin Composition 2

Comparative polyolefin composition 2 (CPC-2) comprises an ethylene-hexene interpolymer, having a density of approximately 0.954 g/cm³, a melt index ($I_2$), measured at 190° C. and 2.16 kg, of approximately 2.3 g/10 minutes, an melt flow ratio ($I_{10}/I_2$) of approximately 11. Additional properties of CPC-2 are reported in Table 2. CPC-2 was prepared via gas phase polymerization in a fluidized bed reactor system.

Comparative Polyolefin Composition 3

Comparative polyolefin composition 3 (CPC-3) comprises an ethylene-based polymer having a density of approximately 0.954 g/cm³, a melt index ($I_2$), measured at 190° C. and 2.16 kg, of approximately 2.2 g/10 minutes, an melt flow ratio ($I_{10}/I_2$) of approximately 8. Additional properties of CPC-3 are reported in Table 2.

TABLE 1

| | Sample | IPC-1 | Reactor 2 Component of IPC-1 | IPC-2 |
|---|---|---|---|---|
| Reactor Configuration | type | dual parallel | single | dual parallel |
| Reactor1 Solvent Feed Flow | kg/hr | 15.8 | | 16.1 |
| Reactor1 Ethylene Feed Flow | kg/hr | 1.8 | | 1.8 |

TABLE 1-continued

| | Sample | IPC-1 | Reactor 2 Component of IPC-1 | IPC-2 |
|---|---|---|---|---|
| Reactor1 Hydrogen Feed Flow | Standard mL/min | 330 | | 369 |
| Reactor1 1-Octene Feed Flow | kg/hr | 0.17 | | 0.10 |
| Reactor1 Feed Temp | °C. | 23.6 | | 20.8 |
| Reactor1 Feed Solvent to Ethylene Ratio | kg/kg | 9.0 | | 9.0 |
| Reactor1 Temp | °C. | 141 | | 140 |
| Reactor1 Oilbath Temp | °C. | 139 | | 140 |
| Reactor1 Catalyst Feed Conc | mmol/kg | 0.1 | | 0.1 |
| Reactor1 Catalyst Feed Flow | g/hr | 49 | | 44 |
| Reactor1 CoCatalyst1 Type | type | RIBS2 | | RIBS2 |
| Reactor1 CoCatalyst1 Feed Conc | mmol/kg | 0.12 | | 0.12 |
| Reactor1 CoCatalyst1 Feed Flow | g/hr | 62 | | 57 |
| Reactor1 CoCatalyst2 Type | type | MMAO3 | | MMAO3 |
| Reactor1 CoCatalyst2 Feed Conc | mmol/kg | 3 | | 3 |
| Reactor1 CoCatalyst2 Feed Flow | g/hr | 50 | | 100 |
| Reactor1 FTnIR Ethylene Concentration | g/L | 15.2 | | 15.1 |
| Reactor1 Ethylene Conversion | % | 73.4 | | 75.1 |
| Reactor1 Viscosity | cPa | 380 | | 353 |
| Reactor2 Solvent Feed Flow | kg/hr | 12.65 | 12.7 | 9.27 |
| Reactor2 Ethylene Feed Flow | kg/hr | 2.8 | 2.8 | 2.1 |
| Reactor2 Hydrogen Feed Flow | Standard mL/min | 800 | 800 | 700 |
| Reactor2 1-Octene Feed Flow | kg/hr | 0 | 0 | 0 |
| Reactor2 Feed Temp | °C. | 7.6 | 7.6 | 4.8 |
| Reactor2 Feed Solvent to Ethylene Ratio | kg/kg | 4.5 | 4.5 | 4.5 |
| Reactor2 Temp | °C. | 200 | 199 | 200 |
| Reactor2 Oilbath Temp | °C. | 191 | 192 | 191 |
| Reactor2 Catalyst Conc | mmol/kg | 0.02 | 0.02 | 0.02 |
| Reactor2 Catalyst Feed Flow | g/hr | 24 | 30 | 23 |
| Reactor2 CoCatalyst1 Type | type | RIBS2 | RIBS2 | RIBS2 |
| Reactor2 CoCatalyst1 Conc | mmol/kg | 0.03 | 0.03 | 0.03 |
| Reactor2 CoCatalyst1 Flow | g/kg | 24 | 30 | 23 |
| Reactor2 CoCatalyst2 Type | type | MMAO3 | MMAO3 | MMAO3 |
| Reactor2 CoCatalyst2 Feed Conc | mmol/kg | 3 | 3 | 3 |
| Reactor2 CoCatalyst2 Feed Flow | g/hr | 40 | 40 | 40 |
| Reactor2 FTnIR Ethylene Concentration | g/L | 7.7 | 7.9 | 8.0 |
| Overall Ethylene Conversion | % | 93.1 | 92.5 | 92.8 |
| Reactor2 Viscosity | cPa | 28 | 31 | 25 |

TABLE 2

| Property | Test Method | Units | IPC-1 | IPC-2 | CPC-1 | CPC-2 | CPC-3 |
|---|---|---|---|---|---|---|---|
| Density | ASTM D792 Method B | g/cm$^3$ | 0.954 | 0.953 | 0.956 | 0.954 | 0.954 |
| $I_2$ | ASTM D1238 | dg/min | 2.6 | 1.5 | 1.4 | 2.3 | 2.2 |
| $I_{10}$ | ASTM D1238 | dg/min | 25.5 | 13.5 | 17.9 | 25.3 | 18.3 |
| $I_{21}$ | ASTM D1238 | dg/min | 117.6 | 60.9 | 93.4 | 111.1 | 66.8 |
| $I_{10}/I_2$ | | | 10 | 9 | 13 | 11 | 8 |
| $I_{21}/I_2$ | | | 46 | 40 | 67 | 48 | 30 |
| $M_n$ | Conventional GPC | | 21,576 | 23,115 | 8,561 | 11,724 | 11,693 |
| $M_w$ | Conventional GPC | | 90,213 | 103,224 | 121,348 | 107,509 | 106,732 |
| $M_w/M_n$ | Conventional GPC | | 4.2 | 4.5 | 14.2 | 9.2 | 9.1 |
| $M_z$ | Conventional GPC | | 279,083 | 303,753 | 636,554 | 530,446 | 490,096 |
| Tm1 | DSC | °C. | 131.3 | 131.2 | 130.7 | 131.1 | 131.7 |
| Heat of Fusion | DSC | J/g | 211 | 208 | 212 | 212 | 211 |
| Tc1 | DSC | °C. | 117.5 | 117.8 | 117.4 | 117.4 | 117.9 |
| Heat of Cryst. | DSC | J/g | 210 | 210 | 214 | 213 | 212 |
| Tan Delta 0.1 radians per second | DMS | N/A | 17.4 | 12.0 | 5.3 | 7.5 | 8.4 |
| η* @ 0.1 rad/s | DMS | Pa.s | 3,692 | 5,896 | 8,105 | 4,802 | 4,557 |
| [η* @ 0.1 (rad/s)]/[η* @ 100 (rad/s)] | DMS | | 4.4 | 5.1 | 8.6 | 5.9 | 4.3 |
| Width at ½ height | CEF | °C. | 4.40 | 4.20 | 3.60 | 3.40 | 3.20 |
| Width at 1/10 height | CEF | °C. | 15.0 | 8.0 | 13.2 | 11.0 | 7.8 |
| Standard Deviation Half Height | CEF | °C. | 5.41 | 4.49 | 9.44 | 8.80 | 8.26 |

TABLE 2-continued

| Property | Test Method | Units | IPC-1 | IPC-2 | CPC-1 | CPC-2 | CPC-3 |
|---|---|---|---|---|---|---|---|
| Width/Std. Dev. | CEF | | 0.814 | 0.935 | 0.382 | 0.386 | 0.387 |
| CDC | CDC | | 117 | 102 | 249 | 246 | 245 |
| Vinyls/1000C. | IR Method | | Less than 0.15 | Less than 0.15 | 0.14 | 0.2 | 0.21 |
| Oligomer Content | GC | ug/g | 47 | 38 | 415 | 280 | 327 |
| ESCR, 10% Igepal, F50 | ASTM D1693-B | h | 274 | 242 | 169 | 67 | 23 |

Test Methods

Test methods include the following:

Density

Samples that are measured for density are prepared according to ASTM D4703. Measurements are made within one hour of sample pressing using ASTM D792, Method B.

Melt Index

Melt index ($I_2$) is measured in accordance with ASTM D1238, Condition 190° C./2.16 kg, and is reported in grams eluted per 10 minutes. Melt flow rate ($I_{10}$) is measured in accordance with ASTM D1238, Condition 190° C./10 kg, and is reported in grams eluted per 10 minutes.

Differential Scanning Calorimetry (DSC)

DSC can be used to measure the melting and crystallization behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (~25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 150° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are peak melting temperature ($T_m$), peak crystallization temperature ($T_c$), heat of fusion ($H_f$) in Joules per gram and heat of crystallization (J/g) using Equation 1.

The heat of fusion ($H_f$) and the peak melting temperature are reported from the second heat curve. Peak crystallization temperature and heat of crystallization is determined from the cooling curve.

Dynamic Mechanical Spectroscopy (DMS) Frequency Sweep

Samples were compression-molded into 3 mm thick x 25 mm diameter circular plaques at 177° C. for 5 minutes under 10 MPa pressure in air. The sample was then taken out of the press and placed on the counter to cool.

Constant temperature frequency sweep measurements were performed on an ARES strain controlled rheometer (TA Instruments) equipped with 25 mm parallel plates, under a nitrogen purge. For each measurement, the rheometer was thermally equilibrated for at least 30 minutes prior to zeroing the gap. The sample was placed on the plate and allowed to melt for five minutes at 190° C. The plates were then closed to 2 mm, the sample trimmed, and then the test was started. The method has an additional five minute delay built in, to allow for temperature equilibrium. The experiments were performed at 190° C. over a frequency range of 0.1-100 rad/s at five points per decade interval. The strain amplitude was constant at 10%. The stress response was analyzed in terms of amplitude and phase, from which the storage modulus (G'), loss modulus (G"), complex modulus (G*), dynamic complex viscosity ($\eta^*$), and tan ($\delta$) or tan delta were calculated.

Conventional Gel Permeation Chromatography (GPC)

The GPC system consists of either a Polymer Laboratories Model PL-210 or a Polymer Laboratories Model PL-220 instrument equipped with a refractive index (RI) concentration detector. The column and carousel compartments are operated at 140° C. Three Polymer Laboratories 10-μm Mixed-B columns are used with the solvent 1,2,4-trichlorobenzene. The samples are prepared at a concentration of 0.1 g of polymer in 50 milliliters of solvent. The solvent used to prepare the samples contains 200 ppm of the antioxidant butylated hydroxytoluene (BHT). Samples are prepared by agitating lightly for four hours at 160° C. The injection volume used is 200 microliters and the flow rate is 1.0 ml/min Calibration of the GPC column set is performed with twenty one narrow molecular weight distribution polystyrene standards purchased from Polymer Laboratories.

The polystyrene standard peak molecular weights ($M_{PS}$) are converted to polyethylene molecular weight ($M_{PE}$) using Equation 1. The equation is described in Williams and Ward, J. Polym. Sci., Polym. Letters, 6, 621 (1968)):

$$M_{PE} = A \times (M_{PS})^B \quad \text{Equation 1}$$

Where A has a value of 0.4316 and B is equal to 1.0.

A third order polynomial is determined to build the logarithmic molecular weight calibration as a function of elution volume.

Polyethylene equivalent molecular weight calculations were performed using PolymerChar "GPC One" software. The number average molecular weight (Mn), weight average molecular weight (Mw), and z-average molecular weight (Mz) was calculated by inputting the GPC results in equations 2 to 4:

$$\overline{Mn} = \frac{\sum\limits_i RI_i}{\sum\limits_i (RI_i / M_{PE,i})} \quad \text{Equation 2}$$

$$\overline{Mw} = \frac{\sum_{i}(RI_i * M_{PE,i})}{\sum_{i} RI_i} \quad \text{Equation 3}$$

$$\overline{Mz} = \frac{\sum_{i}(RI_i * M_{PE,i}^2)}{\sum_{i}(RI_i * M_{PE,i})} \quad \text{Equation 4}$$

Where $RI_i$ and $M_{PE,i}$ are the concentration detector baseline corrected response and conventional calibrated polyethylene molecular weight for the $i^{th}$ slice of the concentration response, elution volume paired data set. The precision of the weight-average molecular weight $\Delta Mw$ is <2.6%.

The MWD is expressed as the weight average molecular weight (Mw) divided by the number average molecular weight (Mn).

The GPC column set is calibrated by running 21 narrow molecular weight distribution polystyrene standards. The molecular weight (MW) of the standards ranges from 580 to 8,400,000, and the standards are contained in 6 "cocktail" mixtures. Each standard mixture has at least a decade of separation between individual molecular weights. The standard mixtures are purchased from Polymer Laboratories. The polystyrene standards are prepared at 0.025 g in 50 mL of solvent for molecular weights equal to or greater than 1,000,000 and 0.05 g in 50 mL of solvent for molecular weights less than 1,000,000. The polystyrene standards were dissolved at 80° C. with gentle agitation for 30 minutes. The narrow standards mixtures are run first and in order of decreasing highest molecular weight component to minimize degradation.

CEF Method

Comonomer distribution analysis is performed with Crystallization Elution Fractionation (CEF) (PolymerChar in Spain, (B Monrabal et al, Macromol. Symp., 257, 71-79, 2007). Ortho-dichlorobenzene (ODCB) with 600 ppm antioxidant butylated hydroxytoluene (BHT) is used as solvent. Sample preparation is done with auto sampler at 160° C. for 2 hours under shaking at 4 mg/ml (unless otherwise specified). The injection volume is 300 µl. The temperature profile of CEF is: crystallization at 3° C./min from 110° C. to 30° C., the thermal equilibrium at 30° C. for 5 minutes, elution at 3° C./min from 30° C. to 140° C. The flow rate during crystallization is at 0.052 ml/min. The flow rate during elution is at 0.50 ml/min. The data is collected at one data point/second.

CEF column is packed by the Dow Chemical Company with glass beads at 125 µm±6% (MO-SCI Specialty Products) with 1/8 inch stainless tubing. Glass beads are acid washed by MO-SCI Specialty with the request from the Dow Chemical Company. Column volume is 2.06 ml. Column temperature calibration is performed by using a mixture of NIST Standard Reference Material Linear polyethylene 1475a (1.0 mg/ml), and Eicosane (2 mg/ml) in ODCB. Temperature is calibrated by adjusting elution heating rate so that NIST linear polyethylene 1475a has a peak temperature at 101.0° C., and Eicosane has a peak temperature of 30.0° C. The CEF column resolution is calculated with a mixture of NIST linear polyethylene 1475a (1.0 mg/ml) and hexacontane (Fluka, purum, ≥97.0%, 1 mg/ml). A baseline separation of hexacontane and NIST polyethylene 1475a is achieved. The area of hexacontane (from 35.0 to 67.0° C.) to the area of NIST 1475a from 67.0 to 110.0° C. is 50 to 50, the amount of soluble fraction below 35.0° C. is <1.8 wt %. The CEF column resolution is defined in equation 1, where the column resolution is 6.0.

$$\text{Resolution} = \frac{\text{Peak temperature of NIST 1475a} - \text{Peak Temperature of Hexacontane}}{\text{Half-height Width of NIST 1475a} + \text{Half-height Width of Hexacontane}} \quad \text{Equation 1}$$

Determination of Half Height and One Tenth Height of the CEF Elution Profile

The CEF instrument is calibrated according to the CEF Method described herein, and a plot of the relative IR detector signal is made as a function of temperature. A single baseline is subtracted from the IR measurement signal in order create a relative mass-elution profile plot starting and ending at zero relative mass at its lowest and highest elution temperatures (typically between 25° C. and 110° C.). For convenience, this plot (FIG. 1) plotted as a normalized quantity with an area equivalent to 100. In the relative mass-elution profile plot, peaks that represent an area of at least 25% of the total integrated signal between 35° C. and 110° C. degrees are assigned. Any peaks that do not return to the baseline by at least 10% of the relative mass-elution height (connected by more than 10% height at their lowest point), are defined as a single peak (no deconvolution or similar numerical methods are used to mathematically separate convoluted peaks). Each separate peak is then measured for width in ° C. at 50% of the maximum height of the peak in the mass-elution profile plot. Each separate peak is then measured for width ° C. at 10% of the maximum height in the mass-elution profile plot.

CDC Method

Comonomer distribution constant (CDC) is calculated from comonomer distribution profile by CEF. CDC is defined as Comonomer Distribution Index divided by Comonomer Distribution Shape Factor multiplying by 100 as shown in Equation 1.

$$CDC = \frac{\text{Comonomer Distrubution Index}}{\text{Comonomer Distribution Shape Factor}} = \frac{\text{Comonomer Distribution Index}}{\text{Half Width/Stdev}} * 100 \quad \text{Equation 1}$$

Comonomer distribution index stands for the total weight fraction of polymer chains with the comonomer content ranging from 0.5 of median comonomer content ($C_{median}$) and 1.5 of $C_{median}$ from 35.0 to 119.0° C. Comonomer Distribution Shape Factor is defined as a ratio of the half width of comonomer distribution profile divided by the standard deviation of comonomer distribution profile from the peak temperature ($T_p$).

CDC is calculated from comonomer distribution profile by CEF, and CDC is defined as Comonomer Distribution Index divided by Comonomer Distribution Shape Factor multiplying by 100 as shown in Equation 4, and wherein Comonomer distribution index stands for the total weight fraction of polymer chains with the comonomer content ranging from 0.5 of median comonomer content ($C_{median}$) and 1.5 of $C_{median}$ from 35.0 to 119.0° C., and wherein Comonomer Distribution Shape Factor is defined as a ratio of the half width of comonomer distribution profile divided by the standard deviation of comonomer distribution profile from the peak temperature (Tp).

CDC is calculated according to the following steps:

(A) Obtain a weight fraction at each temperature (T) ($w_T(T)$) from 35.0° C. to 119.0° C. with a temperature step increase of 0.2° C. from CEF according to Equation 2.

$$\int_{35}^{119.0} w_T(T)dT = 1 \qquad \text{Equation 2}$$

(B) Calculate the median temperature ($T_{median}$) at cumulative weight fraction of 0.500, according to Equation 3.

$$\int_{35}^{T_{median}} w_T(T)dT = 0.5 \qquad \text{Equation 3}$$

(C) Calculate the corresponding median comonomer content in mole % ($C_{median}$) at the median temperature ($T_{median}$) by using comonomer content calibration curve according to Equation 4.

$$\ln(1 - cononomercontent) = -\frac{207.26}{273.12+T} + 0.5533 \qquad \text{Equation 4}$$
$$R^2 = 0.997$$

(D) Construct a comonomer content calibration curve by using a series of reference materials with known amount of comonomer content, i.e., eleven reference materials with narrow comonomer distribution (mono-modal comonomer distribution in CEF from 35.0 to 119.0° C.) with weight average Mw of 35,000 to 115,000 (measured via conventional GPC) at a comonomer content ranging from 0.0 mole % to 7.0 mole % are analyzed with CEF at the same experimental conditions specified in CEF experimental sections;

(E) Calculate comonomer content calibration by using the peak temperature ($T_p$) of each reference material and its comonomer content. The calibration is calculated from each reference material as shown in Equation 4 wherein: $R^2$ is the correlation constant.

(F) Calculate Comonomer Distribution Index from the total weight fraction with a comonomer content ranging from $0.5*C_{median}$ to $1.5*C_{median}$, and if $T_{median}$ is higher than 98.0° C., Comonomer Distribution Index is defined as 0.95.

(G) Obtain Maximum peak height from CEF comonomer distribution profile by searching each data point for the highest peak from 35.0° C. to 119.0° C. (if the two peaks are identical, then the lower temperature peak is selected); half width is defined as the temperature difference between the front temperature and the rear temperature at the half of the maximum peak height, the front temperature at the half of the maximum peak is searched forward from 35.0° C., while the rear temperature at the half of the maximum peak is searched backward from 119.0° C., in the case of a well defined bimodal distribution where the difference in the peak temperatures is equal to or greater than the 1.1 times of the sum of half width of each peak, the half width of the inventive ethylene-based polymer composition is calculated as the arithmetic average of the half width of each peak; and (H) Calculate the standard deviation of temperature (Stdev) according Equation 5

$$Stdev = \sqrt{\sum_{35.0}^{119.0}(T-T_p)^2 * w_T(T)} \qquad \text{Equation 5}$$

Creep Zero Shear Viscosity Measurement Method

Zero-shear viscosities are obtained via creep tests that were conducted on an AR-G2 stress controlled rheometer (TA Instruments; New Castle, Del.) using 25-mm-diameter parallel plates at 190° C. The rheometer oven is set to test temperature for at least 30 minutes prior to zeroing fixtures. At the testing temperature a compression molded sample disk is inserted between the plates and allowed to come to equilibrium for 5 minutes. The upper plate is then lowered down to 50 μm above the desired testing gap (1.5 mm) Any superfluous material is trimmed off and the upper plate is lowered to the desired gap. Measurements are done under nitrogen purging at a flow rate of 5 L/min Default creep time is set for 2 hours.

A constant low shear stress of 20 Pa is applied for all of the samples to ensure that the steady state shear rate is low enough to be in the Newtonian region. The resulting steady state shear rates are in the range of $10^{-3}$ to $10^{-4}$ s$^{-1}$ for the samples in this study. Steady state is determined by taking a linear regression for all the data in the last 10% time window of the plot of log (J(t)) vs. log(t), where J(t) is creep compliance and t is creep time. If the slope of the linear regression is greater than 0.97, steady state is considered to be reached, then the creep test is stopped. In all cases in this study the slope meets the criterion within 2 hours. The steady state shear rate is determined from the slope of the linear regression of all of the data points in the last 10% time window of the plot of ϵ vs. t, where ϵ is strain. The zero-shear viscosity is determined from the ratio of the applied stress to the steady state shear rate.

In order to determine if the sample is degraded during the creep test, a small amplitude oscillatory shear test is conducted before and after the creep test on the same specimen from 0.1 to 100 rad/s. The complex viscosity values of the two tests are compared. If the difference of the viscosity values at 0.1 rad/s is greater than 5%, the sample is considered to have degraded during the creep test, and the result is discarded.

Zero-Shear Viscosity Ratio (ZSVR) is defined as the ratio of the zero-shear viscosity (ZSV) of the branched polyethylene material to the ZSV of the linear polyethylene material at the equivalent weight average molecular weight (Mw-gpc) according to the following Equations 1 and 2

$$ZSVR = \frac{\eta_{0B}}{\eta_{0L}} \qquad \text{Equation 1}$$

$$\eta_{0L} = 2.29 \times 10^{-15} M_{w-gpc}^{3.65} \qquad \text{Equation 2}$$

The ZSV value is obtained from creep test at 190° C. via the method described above. The Mw-gpc value is determined by the conventional GPC method (Equation 3). The correlation between ZSV of linear polyethylene and its Mw-gpc was established based on a series of linear polyethylene reference materials. A description for the ZSV-Mw relationship can be found in the ANTEC proceeding: Karjala, Teresa P., Sammler, Robert L., Mangnus, Marc A., Hazlitt, Lonnie G., Johnson, Mark S., Hagen, Charles M. Jr., Huang, Joe W. L., Reichek, Kenneth N., "Detection of low levels of long-chain branching in polyolefins", Annual Technical Conference—Society of Plastics Engineers (2008), 66th 887-891.

$^1$H NMR Method 3.26 g of stock solution is added to 0.133 g of polyolefin sample in 10 mm NMR tube. The stock solution is a mixture of tetrachloroethane-$d_2$ (TCE) and perchloroethylene (50:50, w:w) with 0.001M $Cr^{3+}$. The solution in the tube is purged with $N_2$ for 5 minutes to reduce the amount of oxygen. The capped sample tube is left at room temperature overnight to swell the polymer sample. The sample is dissolved at 110° C. with shaking. The samples are free of the additives that may contribute to unsaturation, e.g. slip agents such as erucamide.

The $^1$H NMR are run with a 10 mm cryoprobe at 120° C. on Bruker AVANCE 400 MHz spectrometer.

Two experiments are run to get the unsaturation: the control and the double presaturation experiments.

For the control experiment, the data is processed with exponential window function with LB=1 Hz, baseline was corrected from 7 to −2 ppm. The signal from residual $^1$H of TCE is set to 100, the integral $I_{total}$ from −0.5 to 3 ppm is used as the signal from whole polymer in the control experiment. The number of $CH_2$ group, $NCH_2$, in the polymer is calculated as following:

$$NCH_2 = I_{total}/2 \qquad \text{Equation 1}$$

For the double presaturation experiment, the data is processed with exponential window function with LB=1 Hz, baseline was corrected from 6.6 to 4.5 ppm. The signal from residual $_1$H of TCE is set to 100, the corresponding integrals for unsaturations ($I_{vinylene}$, $I_{trisubstituted}$, $I_{vinyl}$ and $I_{vinylidene}$) were integrated based on the region shown in FIG. 6. The number of unsaturation unit for vinylene, trisubstituted, vinyl and vinylidene are calculated:

$$N_{vinylene} = I_{vinylene}/2 \qquad \text{Equation 2}$$

$$N_{trisubstituted} = I_{trisubstitute} \qquad \text{Equation 3}$$

$$N_{vinyl} = I_{vinyl}/2 \qquad \text{Equation 4}$$

$$N_{vinylidene} = I_{vinylidene}/2 \qquad \text{Equation 5}$$

The unsaturation unit/1,000carbons are calculated as following:

$$N_{vinylene}/1{,}000C = (N_{vinylene}/NCH_2)*1{,}000 \qquad \text{Equation 6}$$

$$N_{trisubstituted}/1{,}000C = (N_{trisubstituted}/NCH_2)*1{,}000 \qquad \text{Equation 7}$$

$$N_{vinyl}/1{,}000C = (N_{vinyl}/NCH_2)*1{,}000 \qquad \text{Equation 8}$$

$$N_{vinylidene}/1{,}000C = (N_{vinylidene}/NCH_2)*1{,}000 \qquad \text{Equation 9}$$

The chemical shift reference is set at 6.0 ppm for the $^1$H signal from residual proton from TCT-d2. The control is run with ZG pulse, TD 32768, NS 4, DS 12, SWH 10,000 Hz, AQ 1.64s, D1 14s. The double presaturation experiment is run with a modified pulse sequence, O1P 1.354 ppm, O2P 0.960 ppm, PL9 57 db, PL21 70 db, TD 32768, NS 200, DS 4, SWH 10,000 Hz, AQ 1.64s, D1 1 s, D13 13s.

$^{13}$C NMR Method

The samples were prepared by adding approximately 2.74 g of tetrachloroethane-$d_2$ containing 0.025 M Cr $(AcAc)_3$ to 0.2 g sample in a Norell 1001-7 10 mm NMR tube. Oxygen was removed by manually purging tubes with nitrogen using a Pasteur pipette for 1 minute. The samples were dissolved and homogenized by heating the tube and its contents to ~150° C. using a heating block with minimal use of heat gun. Each sample was visually inspected to ensure homogeneity. Samples were thoroughly mixed immediately prior to analysis, and were not allowed to cool before insertion into the heated NMR probe. This is necessary to ensure the sample is homogeneous and representative of the whole. The data were collected using a Bruker 400 MHz spectrometer equipped with a Bruker cryoprobe. The data were acquired using 160 scans, a 6 sec pulse repetition delay with a sample temperature of 120° C. All measurements were made on non-spinning samples in locked mode. Samples were allowed to thermally equilibrate for 7 minutes prior to data acquisition. The $^{13}$C NMR chemical shifts were internally referenced to the EEE triad at 30 ppm.

Oligomers in PE Using GC

About 5 grams of sample is weighed and transferred to a glass bottle. A pipette is used to deliver 20 mL of methylene chloride to the glass bottle. The bottle is capped with a Teflon lined lid and the contents are shaken for 24 hours at room temperature. After extraction an aliquot of methylene chloride is removed and placed into a GC autosampler vial. The sample extracts are analyzed by GC with a flame ionization detector along with a hydrocarbon standard. Total peak area is determined for peaks between methylene chloride and C44H90. The peaks for Irgafos 168, oxidized I-168 and Irganox 1076 are excluded. The concentration in parts per million is calculated including the range from $C_{10}$-$C_{44}$ using an external standard calibration with a C20H42 calibration standard.

Vinyls, and Unsaturation Determination by IR Method

Pellets are pressed into a film and film is analyzed by FTIR to determine concentration of each in sample. Results are reported as the number per 1000 carbons. Procedures were conducted as per ASTM D6248 Standard Test Method for Vinyl and Trans Unsaturation in Polyethylene by Infrared Spectrophotometry.

We claim:

1. A polyolefin composition suitable for injection molding applications comprising:
an ethylene/α-olefin interpolymer composition comprising: (a) from 25 to 50 percent by weight of a first ethylene/α-olefin copolymer fraction having a density in the range of from 0.924 to 0.937 g/cm$^3$, a melt index ($I_2$) in the range of from 0.03 to 0.3 g/10 min, (b) from 50 to 75 percent by weight of a second ethylene homopolymer fraction having a density in the range of from greater than 0.960 g/cm$^3$, a melt index ($I_2$) in the range of from 100 to 180 g/10 minutes, wherein said ethylene/α-olefin interpolymer composition has a density in the range of from 0.950 to 0.958 g/cm$^3$, a melt index ($I_2$) in the range of from 1.0 g/10 min to 3.5 g/10 min, a zero shear viscosity ratio (ZSVR) in the range of from 1.01 to 2.5, a molecular weight distribution ($M_w/M_n$) in the range of from 2.0 to 4.0, and tan delta at 0.1 radian/second and 190° C. in the range of from 9 to 50, wherein said ethylene/α-olefin interpolymer composition has at least 1 peak on elution profile via crystallization elution fractionation (CEF) procedure, wherein said peak comprises at least 95 weight percent of the total area of the elution profile, wherein said elution temperature peak is at an elution temperature greater than 95° C., and wherein the width of the elution temperature peak at 50 percent peak height is greater than 4° C. and less than 6° C., and wherein the standard deviation of the temperature is less than 6° C.

2. The polyolefin composition of claim 1, wherein said ethylene/α-olefin interpolymer composition characterized by one or more of the followings:
  a. has a vinyl unsaturation of less than 0.15 vinyls per one thousand carbon atoms present in the backbone of the ethylene/α-olefin interpolymer composition; and/or
  b. has a tan delta at 0.1 radian/second, determined at 190° C., in the range of from 9 to 50;
  c. has CDC in the range of from 150 or less;
  d. has a ESCR F50 failure time of at least 150 hours, as determined by ASTM 1693 Method B in 10% aqueous Igepal; and/or
  e. has a oligomer, i.e. $C_{10}$ to $C_{44}$, content of less than 100 ppm.

3. The polyolefin composition of claim 1 further comprising one or more ethylene polymers, or one or more propylene based polymers, or combinations thereof.

4. A closure device comprising the polyolefin composition of claim 1.

* * * * *